United States Patent [19]

Basbøll

[11] Patent Number: 5,648,227

[45] Date of Patent: Jul. 15, 1997

[54] METHOD OF DETECTING MICROORGANISMS

[75] Inventor: Ole Basbøll, Birkerød, Denmark

[73] Assignee: Amdex A/S, Copenhagen, Denmark

[21] Appl. No.: 302,828

[22] PCT Filed: Mar. 25, 1993

[86] PCT No.: PCT/DK93/00112

§ 371 Date: Oct. 14, 1994

§ 102(e) Date: Oct. 14, 1994

[87] PCT Pub. No.: WO93/19372

PCT Pub. Date: Sep. 30, 1993

[30] Foreign Application Priority Data

Mar. 25, 1992 [DK] Denmark ............................ 0395/92

[51] Int. Cl.$^6$ ............................ G01N 33/569; C07K 16/12
[52] U.S. Cl. ............................ 435/7.32; 435/5; 435/31; 435/29; 435/340; 530/388.4
[58] Field of Search ............................ 435/5, 7.32, 31, 435/29, 240.27; 530/388.4, 388.3, 388.5

[56] References Cited

U.S. PATENT DOCUMENTS 5,077,192  12/1991  Liang et al. ............................ 435/5

OTHER PUBLICATIONS

Nair, et al., *International Journal of Leprosy and Other Mycobacterial Diseases*, vol. 58, No. 3, pp. 540–547, Sep. 1990.

*Primary Examiner*—Toni R. Scheiner
*Attorney, Agent, or Firm*—Watson Cole Stevens Davis, P.L.L.C.

[57] ABSTRACT

Method for detecting the presence or absence of a viable microorganism in a sample which has been subjected to a sterilization process, whereby the sample is contacted with an antibody which specifically recognizes and binds an indicator epitope found on the surface of an intact viable microorganism, but not on the surface of a microorganism killed by the sterilization process.

14 Claims, No Drawings

METHOD OF DETECTING MICROORGANISMS

The present invention relates to a method of detecting the presence or absence of viable microorganisms in a sample.

More particularly, it relates to the use of suitable antibodies which specifically recognise and bind an epitope located on the surface of intact viable microorganisms.

There is a need to detect viable microorganisms in food samples, water, air, industrial products, human clinical and animal samples as rapidly as possible. It is also desirable to identify genus and species at the same time.

A number of ways to improve upon the traditional culture methods have more recently been developed. Thus, to accelerate the bacterial identification process, highly specific polyclonal and preferably monoclonal antibodies have been developed that can be used in immunodiagnostic tests, such as an ELISA test. In the ELISA test a sample of culture medium is added directly to an antibody coated tube and the specific microorganisms in the culture medium are thus immobilised onto the surface of the coated tube, where they can be detected by means of a second, labelled antibody.

The ELISA test suffers a disadvantage compared to the extended culture procedure discussed below. The sensitivity of the best ELISA tests currently available is about $10^4$ to $10^5$ organisms per milliliter. At microorganism concentrations below this range the test will be negative and the microorganisms will not be detected. In contrast, culture procedures should be able to detect a single bacterium. Since the ELISA tests currently available are a relatively less sensitive technique, they still require one or more culture steps in order to enrich the number of microorganisms present in the sample before the ELISA test is carried out. Often these additional culture steps can take 16 hours or more.

The traditional culture techniques are slow and are now being superseded by rapid detection methods based particularly on ultra-sensitive DNA probe and DNA amplification techniques. DNA amplifiers, such as the polymerase chain reaction (PCR), the ligase chain reaction (LCR) and the DNA/RNA systems, such as NASBA or 3SR, can theoretically detect a single microorganism, and can provide a species identification at the same time.

In a production process, such as the preparation of a pharmaceutical or a foodstuff, there is often incorporated a sterilisation step to kill the microorganisms present in the product. Sterilisation steps commonly employ heat, extremes of pH, salt, bactericidal chemicals, irradiation or exposure to ethylene oxide. Less aggressive conditions are also commonly used, such as pasteurisation. Any microorganisms present in, or on, the product will not be viable after sterilisation and a subsequent culture procedure will report a negative result. However, the culture procedure is slow, and alternatives, such as ultrasensitive DNA probes and DNA amplifiers, cannot distinguish between live and dead cells and also cannot distinguish between live cells and extraneous nucleic acid from disrupted (dead) cells. Hence, these detection techniques are undesired because they are tedious and slow or because they can report false positives after sterilisation procedures, which has serious commercial implications in the food and manufacturing industries and serious medical implications in healthcare.

One way of capturing microorganisms in a dispersed food sample, in a clinical sample, e.g. blood, urine, or in a wash eluent from a surface is to pass a volume of the fluid through a controlled pore or depth filter membrane, to wash the membrane and then to detect the entrapped microorganisms. The disadvantages of this approach are that until now intact viable and intact dead cells could only be distinguished by culture techniques and, as a secondary issue, dispersed particulate samples such as foodstuffs, red cells in whole blood, or tissue material in urine can block the filter rapidly.

It is well known that microorganisms are disrupted on heating to high temperatures e.g. boiling, as this is often used to release the nucleic acid from the cell. It is also known that boiling will denature antigens on the microorganisms' surface so that they are no longer recognised by antibodies. The issue of intact but dead or non-viable organisms and the false positives they could cause in sensitive tests has not been discussed in any documents found so far.

Liang et al. disclose in U.S. Pat. No. 5,077,192 the use of an antibody to capture a microorganism, such as a virus, from a small serum sample; the antibody is preferably bound to microparticles. After washing, the DNA in the virus is exposed by heating and a PCR process amplifies the DNA directly. There is no disclosure by Liang et al. of selectively capturing viable viruses or cells and eluting the microorganism intact from the antibody coated solid phase, or exposing the DNA for detection directly.

What is needed is a method of selecting live, intact microorganisms from a sterilised or pasteurised product which method rejects dead, intact cells and the extraneous nucleic acid originating from disrupted cells. Only the viable cells will then be detected by a subsequent high sensitivity detection or identification procedure, such as an ultrasensitive immunoassay, a nucleic acid probe, such as a DNA probe, a nucleic acid amplification procedure, flow cytometry or an optical or electrical biosensor.

Ideally a selection step is required that will result in capturing only intact viable microorganisms, any intact non-viable microorganisms, extraneous nucleic acid and particulate matter from the sample being discarded first. The captured viable microorganisms can then be used directly in a specific detection test.

It has now been found that specific antibodies can recognise epitopes on a surface of an intact and viable microorganism, these epitopes act as indicators of cell viability.

Theoretically, different indicator epitopes will be affected by different sterilisation treatments, i.e. a heat labile indicator epitope will be found on intact viable microorganisms, but after heat treatment, such as pasteurisation, which kills microorganisms without necessarily disrupting them, the epitope has changed and is no longer recognised by the specific antibody. Correspondingly, other sterilisation treatments, such as low pH, high salt and irradiation, will affect other indicator epitopes. The changes of the indicator epitopes are probably caused by denaturation of proteins or dissociation of components on the surface of the microorganism.

Microorganisms that have been rendered non-viable by chemical treatment, e.g. chlorine treatment, will also be expected to show changes in surface indicator epitopes such that they will no longer be recognised by a specific antibody. Changes in surface epitopes can be by direct reaction or indirect mechanisms.

Hence, the antibody can distinguish between intact viable cells and intact dead cells and as a corollary, between intact viable cells and free extraneous DNA. The antibody can be used in aqueous solution or bound to a solid phase material, such as microparticles, microplate wells, test tubes, foams, meshes, membranes or other materials commonly used in diagnostic procedures.

The object of the invention is to provide a method of detecting the presence or absence of a viable microorganism in a sample to be tested which method does not require culturing of the microorganism.

The method according to the invention is characterized in contacting the sample with an antibody which specifically recognises and binds an indicator epitope found only on a surface of an intact viable microorganism and does not bind dead but intact organisms killed by a process, and subsequently optionally eluting the captured microorganism using methods known per se and/or detecting or identifying said microorganism using methods known per se.

The process of the present invention enables culturing steps to be dispensed with and this is of particular importance since culturing can be hazardous if pathogens, such as Salmonella, *Clostridium botulinum* or *Listeria monocytogenes*, are involved. In certain countries, the culturing of microorganisms is not allowed on premises where foodstuffs are being handled. The method of the present invention, which preferably does not involve any culturing step, can thus be carried out on site.

The process of the invention enables 1 to $10^2$ preferably 1 to 10 microorganisms to be detected. When very small numbers of cells are present, such as 1 to $10^2$ organisms in a sample their capture to a solid phase can be improved by recycling the sample several times through a solid phase to which the specific antibody is immobilized.

The term "microorganism" as used herein refers to any type of procaryotic or eucaryotic microscopic organism, such as a bacterium or protozoa, a virus or any kind of higher organism, such as a fungus, a plant, or an animal, which can be maintained in the form of a cell suspension or cell culture.

The term "antibody" as used herein refers to any material which specifically will recognise and bind an antigenic epitope.

The term "viable" as used herein refers to any living intact state of the microorganism, such as active growth or dormancy, from which state it can multiply and/or reproduce itself.

The term "indicator epitope" as used herein refers to any epitope located on the surface of a viable microorganism which can be recognised (and bound) by specific antibodies and which epitope changes or is denatured when the microorganism has been rendered non-viable so that it is no longer recognised by the specific antibody.

More particularly the invention relates to a method of detecting the presence or absence of a viable microorganism, characterized in a) capturing organisms in the sample with the antibody which is bound to a solid phase before or after specific binding with the organism has taken place, b) washing the solid phase to remove non-specifically bound material, c) detecting the organism using any method known per se, including detection directly on the solid phase.

In a preferred embodiment of the invention, the selection of viable microorganisms in a liquid sample of from 0.05 ml to 2000 ml is carried out by a specific antibody bound to a solid phase material of high surface area in intimate contact with a dispersed food sample, such as milk, a beverage, potable water; an industrial effluent or washings from a swab; or a clinical sample, such as whole blood, serum, plasma, urine or sputum, etc. The antibody coated solid phase can be a microwell, a test tube, a dipstick, or preferably a foam or nylon mesh. After an incubation period of from 30 min. to 24 h to capture the microorganisms, the liquid is discarded and the solid phase is preferably washed to remove non-specifically bound material. Then the intact, viable microorganisms are optionally eluted form the solid phase by adding a volume of reagent (such as glycine buffer, pH=2.0) to reverse the antibody/antigen interaction; the elution buffer is then preferably passed through a membrane in order to concentrate the intact microorganisms on a filter surface. The filter, such as a 0.2 μm controlled pore filter of nylon, or cellulose acetate or other polymer or ceramic material, can be used directly in any detection or identification test, such as an ultrasensitive DNA probe or DNA amplification test to detect the entrapped microorganisms by disrupting the cells in situ by heat, enzymic digestion, sonication or solvent, or the DNA can be extracted for subsequent testing.

In summary, a preferred embodiment of the invention is a 2-stage process:

select live, intact microorganisms in a liquid sample by using a specific antibody bound to a high surface area solid phase;

and subsequently detect or identify the microorganism by any method known per se.

The practical advantages of the 2-stage process are that a large sample volume up to about 2000 ml containing dispersed viable, intact microorganisms is quickly discarded and a clean sample of concentrated microorganisms on a filter is provided for subsequent detection. By eluting and concentrating the microorganisms the quantity of expensive DNA probe or DNA amplification reagents used in a final detection step can be minimised.

In an alternative embodiment of the invention the captured, intact viable microorganisms are not eluted from the solid phase after the washing step, but are instead used directly in a DNA probe or DNA amplification test. The cells can be disrupted in situ and the exposed DNA used directly or the DNA can be eluted and purified before use. This alternative embodiment is preferred when the sample volume is small (less than about 5 ml) or when a solid phase, such as microparticles, are used which can be collected by centrifugation or filtration so that only small quantities of the expensive DNA probe or DNA amplification reagents are required in the subsequent detection step.

Intact, viable microorganisms that survive a sterilisation or pasteurisation process are captured by a specific antibody immobilised to a solid phase. The antibody recognises an epitope on the surface of the microorganisms which is not present or is greatly reduced in dead cells. Hence, intact, dead microorganisms and extraneous DNA are not captured by the antibody and are removed by washing. The DNA within the intact, captured cells is then exposed by disrupting the structure and detected by a DNA probe or DNA amplification process. Alternatively, where the original sample volume is large, the captured cells are eluted intact from the solid phase, entrapped and concentrated in a filter and then used directly in a DNA probe or DNA amplification process.

The invention provides a way to avoid false positives resulting from intact dead cells and extraneous DNA from disrupted cells in a DNA probe or DNA amplification test. The invention is also applicable to other ultrasensitive techniques, such as flow cytometry or optical biosensors which would otherwise report false positives from intact, dead or non-viable cells.

The invention further relates to the antibody producing cell line BACO1A 3B4A3 which was deposited with the European Collection of Animal Cell Cultures under ECACC accession No. 91081525, the antibodies obtainable therefrom and use of those antibodies in the method as described herein.

Furthermore, the invention relates to a kit for the detection of viable microorganisms in a sample containing an antibody coated solid phase, buffers for dispersing the sample, washing buffers, elution and/or disruption buffers to expose the nucleic acid in the captured microorganism, hybridisation or amplification reagents to detect or amplify the exposed nucleic acid, or a labelled second antibody to bind to the captured microorganism in an immunoassay, reagents to detect the hybridised probe or the amplified nucleic acid or nucleic acid analogue sequence or the labelled antibody in an immunoassay.

A kit for the detection of live, viable microorganisms which comprises the antibody specific for the indicator epitope bound to a solid phase, presented as microparticles, a microplate well or a high surface area material such as nylon mesh in the form of a dipstick. The sample, which may be used directly or dispersed in a simple buffer such as 0.1M phosphate at neutral pH, is incubated with the antibody coated solid phase for a period sufficient to capture a significant proportion of the microorganisms to the solid phase. Incubation times of 1 to 3 hours are preferred, at ambient temperature (18° C. to 30° C.). The solid phase is then removed from the sample and washed vigorously with a suitable wash solution containing buffer salts, for example 0.1M phosphate and detergents such as 0.1% Tween 20. Washing at least once and preferably three times is required to remove non-specifically bound material. Where the detection method is a DNA probe or DNA amplification system an elution/extraction reagent consisting of a high pH buffer, for example 0.1M sodium hydroxide containing detergents such as 1% SDS is added to the solid phase and in a further incubation, preferably of 1 to 3 hours duration at ambient temperature the microorganisms are released from the surface, the cells are disrupted and the DNA is exposed. In an alternative embodiment an elution buffer only is used, for example 0.4M glycine pH 2.0 and the intact microorganisms are collected on a 0.2 μm filter before the disrupting buffer is added. In the immunoassay detection method a second labelled antibody conjugate is added to the washed solid phase, incubated for 1 to 3 hours at ambient temperature and then the solid phase is washed again using a phosphate/Tween buffer to remove excess conjugate. In the DNA probe or DNA amplification detection method the solution containing the exposed DNA is transferred to a separate tube and then either hybridised to a labelled DNA or DNA analogue probe using known methods (see for example "Nucleic Acid Hybridisation", eds. Hames and Higgins, IRL Press, Oxford, UK, 1985 or amplified using known methods (EP-A-0200362, EP-A-0320308 and Nature, Volume 350, 6313, 91–92) by adding the appropriate amplification reagents and detecting the product by electrophoresis or by a subsequent hybridisation with a labelled probe or by direct detection of the amplified product that has incorporated a label during synthesis. A preferred method of detecting the hybridised labelled probes or the amplified product directly is to employ an indirect labelling method, for example avidin/biotin, and an enzyme label. A kit will therefore contain a substrate for the preferred enzymes alkaline phosphatase or peroxidase. The end measurement of enzyme activity can be made by colorimetric, fluorometric or chemiluminescent means. When a colour is developed by the enzyme a visual inspection is the simplest way to determine whether the sample contained the viable microorganism of interest.

The present invention is further described with reference to the following Examples.

EXAMPLE 1

Preparation of Hybridomas and Antibodies

The preparation of monoclonal antibodies is known and the monoclonal antibodies used in this invention are prepared using the method originally authored by Milstein and Kohler and published in Nature (1975), 256, pps. 495–497. The basic process involves injecting an animal, usually a mouse, with formalin treated Listeria sp. as immunogenic substance. After suitable time for antibody production to the immunogen, the mouse (immunocyte donor: mouse BALB/CXC57BL6F1 hybrid) is sacrificed. Immunocytes are removed from the spleen and fused with myeloma cells (P3X63 Ag 8.6.5.3. Myeloma). Hybridoma cells resulting from this fusion are able to reproduce in vitro, and each expresses genetic information for one specific antibody. The IgG1 antibodies produced from one hybridoma fusion thus will only recognize a single antigenic determinant of the immunogen.

Cells cultured from individual hybridoma cells are screened for production of antibodies to the target antigenic determinant. Those hybridomas positive for the target antigen are further screened to identify those having the highest affinity. The monoclonal antibodies used in the present invention will have an affinity of at least $10^8$ liters/mole.

Monoclonal antibodies displaying all of these characteristics are then screened using actual assay conditions to determine if the assay conditions alter the antibody binding characteristics or affinity, and to screen out those with cross reactivity to possible contaminating antigens.

The hybridoma cell line BAC01A3B4A3 (spherical morphology, growth as suspension) derived from the above fusion produces the antibody B4 which specifically recognizes a heat sensitive epitope on the surface of Listeria cells, which epitope changes its structure under the conditions of pasteurisation. Hybridoma cell line BACO1A3 B4A3 was deposited on Aug. 15, 1991 with the European Collection of Animal Cell Cultures (ECACC), PHLS Centre for Applied Microbiology & Research, Porton Down, Salisbury, Wiltshire, SP4 OJG, United Kingdom. The ECACC has given cell line BACO1A3 B4A3 accession number 91081525.

Additional indications relating to the cell line BACO1A3B4A3 are given in the table below.

ADDITIONAL INDICATIONS

Details of Cell Culture

Identification/Name in full: BACO1A3B4A3

Species and strain: mouse BALB/CXC57 BL 6 F1 hybrid

Organ/Tissue: spleen

Hybridomas

Immunogen: Listeria sp.

Immunocyte donor: Mouse BALB/CXC57 BL 6 F1 hybrid

Immortal partner: P3×63 Ag 8, 6, 5, 3, Myeloma

Product specificity: Antibody against Listeria

Ig class/subclass: IgG1

Additional Information

Cell products/characteristics: Antibody production

Morphology: Spherical

Growth as suspension/attached line: suspension

Cell Storage Conditions

Cell concentration $2-3\times10^6$ cells/ml

Composition of medium: Based on RPMI 1640+10% DMSO

Method of freezing: Manual −70° C. for 7–10 days prior to freezing in liquid Nitrogen Culture Conditions Growth medium: Based on RPMI 1640

% Serum and type: 20% FCS Supplements (and conc.)

Temperature: 37° C. Gaseous phase: gassed incubator 5% $CO_2$

Split ratio (attached): 2–6×10$^5$ cells/ml or (suspension): ✓ cells/ml

Sterility Checks Already Performed

| (delete as appropriate) | | | |
|---|---|---|---|
| Bacteria | Y/N/N | Mycoplasma | Y/N |
| Fungi | Y/N/N | Viruses | YY/N |

Any Other Relevant Information (including technical contact name and telephone/fax if different from depositor) Gurdeep Chadhe Deborah Baron Colin Garner The production of polyclonal antibodies, raised in rabbits is also a well known procedure.

The preparation of antibodies from hybridomas are well known and a practical method is described by Brown, G. and N. R. Ling: Murine monoclonal antibodies, p. 81–104 in Catty, D. (ed.). 1988. Antibodies Volume I, A Practical Approach.

EXAMPLE 2

Evaluation of Antibody Capture of Differentially Treated Listeria Cells

Suspensions of *Listeria monocytogenes* bacteria at a concentration of 10$^6$ cfu/ml were subjected to pasteurisation and boiling treatments as follows:

Suspensions were subjected to a heating regime similar to that experienced during pasteurisation in a factory. Small volumes of the suspensions were placed in glass tubes and rapidly heated to 74° C. by immersion in boiling water. This temperature was maintained as accurately as possible for 20 seconds after which time the tubes were allowed to cool in a controlled manner to 32° C. over a 20 minute period. Suspensions held at 100° C. for 30 minutes were also included in the test.

A further sample of the suspension was left untreated.

These three samples of *Listeria monocytogenes* cell suspensions were then evaluated for capture to particular *Listeria monocytogenes* specific antibodies, including the indicator epitope specific antibody 3B4A3 (B4).

The antibodies were coated on polystyrene microtitre plates (NUNC, Denmark) at a concentration of 10 µg/ml. The three preparations of bacterial suspensions were added to the microtitre wells and incubated for a period of 2 hours. The wells were then washed to remove unbound cells. Then a conjugate of a Listeria genus specific polyclonal antibody from rabbit and horseradish peroxidase was added to the wells and incubated for a further 1 hour. The wells were then washed according to standard procedures to remove unbound material.

The following table shows the absorbance at 450 nm of the substrate (OPD) reflecting the trapping efficiency of polyclonal and B4 antibodies for pasteurised, boiled and untreated cells.

| | Coating Antibody | | | |
|---|---|---|---|---|
| Treatment | Polyclonal* | B1** | B2*** | B4 |
| Pasteurized | 0.28 | 0.27 | 0.23 | 0.20 |
| Boiled | 0.32 | 0.10 | 0.23 | 0.07 |
| Untreated | 0.22 | 0.30 | 0.28 | 0.39 |
| Buffer negative control 0.04 | | | | |

*obtained from rabbit, using standard procedures.
**obtained from Biocode Ltd., mouse monoclonal.
***obtained from Biocode Ltd., mouse monoclonal.

In this experiment the trapping efficiency of B4 for pasteurised cells was approximately 46% of that for live cells and the trapping of boiled cells was not significant.

EXAMPLE 3

Antibody Capture of Listeria Cells by the Antibody B4

The pasteurisation procedure was as described in Example 2. *Listeria monocytogenes* suspensions of 10$^6$, 10$^7$ and 10$^8$ cells per ml were used, and after pasteurisation or boiling for 20 minutes, samples were tested in ELISA. A further dilution was made, and inoculated onto Palcam agar in Petri dishes to test for viability.

The results were as follows:

| | Treatment | | |
|---|---|---|---|
| Concentration of bacteria (cells per ml) | Pasteurised | Boiled | Untreated |
| 10$^8$ | 3.78* | 3.90 | 3.79 |
| 10$^7$ | 1.15 | 0.52 | 1.32 |
| 10$^6$ | 0.14 | 0.12 | 0.26 |
| Buffer | 0.10 | 0.10 | 0.10 |

*Optical density at 450 nm after 1 hour; the conjugate was polyclonal antibody and alkaline phosphatase; the substrate was p-nitro-phenol phosphate.

The results show that discrimination by the antibody between the various treatments is most pronounced at the greatest dilution (10$^6$ cells per ml).

Bacterial colonies were present only on plates inoculated with untreated suspension, showing that the laboratory pasteurisation procedure is effective in killing cells.

EXAMPLE 4

For the detection of *Listeria monocytogenes* cells in soft cheese, the cheese, e.g. Blue Brie, was homogenized in a buffer solution of PBS or PBST (phosphate buffered saline with 0.05% Tween-20) in the ratio 1:9 w/v. Samples of the homogenate containing *Listeria monocytogenes* at 10$^6$ organisms/ml were placed in microtitre plate wells coated with the monoclonal antibody obtained from the cell line BACO1A 3B4A3 deposited with the European Collection of Animal Cell Cultures under ECACC accession No. 91081525.

After an incubation step of 2 hours at room temperature the microtitre plate wells were washed by a standard procedure to remove all but the cells bound to the immobilized antibodies. The DNA within the cells of the microorganism was then exposed by adding a solution containing lysozyme to the wells, incubating briefly at room temperature and then heat lysis at 100° C. in a boiling water bath for 15 minutes.

The exposed DNA of the cells of the microorganism bound to the antibody was then amplified in a PCR process using well known procedures and the amplified *L. monocytogenes* specific DNA was detected by gel electrophoresis and ethidium bromide staining. Positive results were obtained from cheese homogenates containing viable *L. monocytogenes* organisms, negative results were obtained from pasteurised homogenates.

EXAMPLE 5

Detection of Elisa-plate-immobilised *Listeria monocytogenes* Cells by the Monoclonal Antibody B4

Aim

To demonstrate the ability of the B4-antibody to discriminate between immobilized live and dead *Listeria monocytogenes* cells, and the sensitivity at which this is done.

Experimental

General: All incubations are performed at room temperature with agitation unless otherwise specified.

ELISA-plates (Polysorp from Nunc) were coated with cells (live or killed by heat, 100° C. for 30 minutes), 100 µl suspension pr well, using 0.1M sodium phosphate, pH 7.2 (=coating buffer) for dilutions. The next day, plates were blocked with 3 (w/v) % bovine serum albumin in coating buffer, 400 µl per well for 30 minutes. This was followed by one wash with coating buffer, 400 µl per well >5 minutes. Hereafter, plates were incubated with the B4 monoclonal antibody or biotinylated B4 (see details below) diluted in coating buffer for 2 hours. After 4 times wash with 0.1M sodium phosphate, 0.5M NaCl, 0.1 (v/v) % Tween 20, pH 7.2 (using a manual plate-washing device filling wells completely and discarding the liquid again after a few seconds), plates were developed with HRP-coupled rabbit anti-mouse immunoglobulin or HRP-streptavidin (see scheme below) for 1 hour. These reagents were diluted in washing buffer containing 1% sodium caseinate. Hereafter plates were washed again as above and developed with orthophenylenediamine 8 mg/15 ml (buffer containing tablets from Kem-En-Tec A/S) and hydrogen peroxide, 5 µl 30% in 15 ml for 25 minutes (100 µl per well) until it was stopped with 100 µl 1M sulfuric acid. Absorbance was read in a Bio Rad model 450 microplate reader at 490 nm.

Details: Freshly prepared cell suspensions of *Listeria monocytogenes* at $1.9 \times 10^9$ cells/ml from an overnight culture was diluted 1/50, 1/500 and 1/1000 with coating buffer. Second incubations were performed with B4 or biotinylated B4 at 1/200 (corresponding to 5 µg/ml) in coating buffer. Third incubations were performed with HRP-rabbit anti-mouse immunoglobulin (Kem-En-Tec A/S) or HRP-streptavidin (DAKO A/S) at 1/2000 in washing buffer+ casein.

Throughout the examples 5–8 the abbreviation HRP refers to horse radish peroxidase.

Data:

| Cell dilution | Signal, live | Signal, dead |
|---|---|---|
| Buffer negative control: 0.012 (n = 24) | | |
| B4/HRP-rabbit anti-mouse immunoglobulin system: | | |
| 1/50 | 1.596 | 0.152 |
| 1/500 | 0.877 | 0.014* |
| 1/1000 | 0.154 | 0.022* |
|  | (n = 3) | (n = 3) |
|  |  | (*n = 2) |
| Biotin-B4/HRP-streptavidin system: | | |
| 1/50 | 1.032 | 0.162 |
| 1/500 | 0.563 | 0.063 |
| 1/1000 | 0.186 | 0.110 |
|  | (n = 3) | (n = 3) |
| Biotin-B4/HRP-streptavidin system: (using affinity purified B4) | | |
| 1/50 | 0.850 | 0.088 |
| 1/500 | 0.479 | 0.052 |
| 1/1000 | 0.206 | 0.090 |
|  | (n = 3) | (n = 3) |

Conclusion

Best discrimination is seen with underivatized B4 and the Kem-En-Tec HRP-rabbit anti mouse immunoglobulin reagent, showing a 7× live-dead discrimination at 1/1000 which corresponds to $1.9 \times 10^6$ cells/ml.

EXAMPLE 6

The Use of B4 as a Catching Antibody in Combination with HRP-B4 as Detecting Antibody Aim To demonstrate the ability of B4 to act as a catching antibody discriminating between live and dead *Listeria monocytogenes*, using B4 as detecting antibody.

Experimental

General: All incubations are performed at room temperature with agitation unless otherwise specified.

ELISA-plates (Polysorp from Nunc) were coated with B4 antibody, 100 µl pr well, diluted 1/100 (corresponding to 10 µg/ml), using 0.1M sodium phosphate, pH 7.2 (=coating buffer) for dilution. The next day, plates were blocked with 3 (w/v) % bovine serum albumin in coating buffer, 400 µl per well for 30 minutes. This was followed by one wash with coating buffer, 400 µl per well >5 minutes. Hereafter, plates were incubated with the live or dead (heat-treated at 100° C. for 30 minutes) *Listeria monocytogenes* diluted in coating buffer (see below) for 2 hours. After 4 times wash with 0.1M sodium phosphate, 0.5M NaCl, 0.1 (v/v) % Tween 20, pH 7.2 (using a manual plate-washing device filling wells completely and discarding the liquid again after a few seconds), plates were developed with HRP-coupled B4 or biotinylated B4 for one hour. With biotinylated reagents, this was followed by HRP-streptavidin (Kem-En-Tec A/S) for one hour. These reagent was diluted in washing buffer containing 1% sodium caseinate. Hereafter plates were washed again as above and developed with orthophenylenediamine 8 mg/15 ml (buffer containing tablets from Kem-En-Tec A/S) and hydrogen peroxide, 5 µl 30% for 25 minutes (100 µl per well) until it was stopped with 100 µl 1M sulfuric acid. Absorbance was read in a Bio Rad model 450 microplate reader at 490 nm.

Details: Cells were incubated either undiluted (corresponding to $1.9 \times 10^9$ cells/ml), or diluted 1/10, 1/50, 1/200, 1/500 and 1/1000 in coating buffer. In the third incubation HRP-B4 or biotinylated B4 was used at 1/500 in washing buffer+casein. For biotinylated reagents a fourth incubation was performed with HRP-streptavidin (Kem-En-Tec A/S), 1/1000 in washing buffer+casein.

Data

Buffer negative
control: 0.047 (n = 36)
1→3 layer controls: 0.049 (n = 12) (HRP-B4)
0.108 (n = 6) (Biotin-B4/HRP-streptavidin)
0.065 (n = 6) (Biotin-B4 (affinity-purified B4)/ HRP-streptavidin)
Live cells: 1/500 and 1/1000 dilutions were in all cases at 1→3 layer level (=dead cell level) or below.

|  | HRP-B4 | Biotin-B4/ HRP-strept-avidin | Biotin-B4 (affinity-purified B4)/ HRP-streptavidin |
| --- | --- | --- | --- |
| Undiluted | 0.060 | 0.134 | 0.060 |
| 1/10 | 1.531 | 1.857 | 0.459 |
| 1/50 | 0.746 | 1.433 | 0.610 |
| 1/200 | 0.095 | 0.201 | 0.084 |
|  | (n = 6) | (n = 3) | (n = 3) |
| Dead cells: | 0.049 | 0.108 | 0.065 |

Conclusion

Dead cell levels corresponds to 1→3 layer controls. A near-total quenching of the signal is seen with undiluted cell-suspensions (corresponding to $1.9 \times 10^9$ cells/ml). Discrimination is seen in these systems at the 1/200 (corresponds to $9.5 \times 10^6$ cells/ml) level.

EXAMPLE 7

Catching of Cells Preincubated with HRP-B4 by Elisa-plate Immobilised Rabbit-Anti Mouse Immunoglogulin Antibody Aim To demonstrate the selective binding of HRP-B4 to live as opposed to dead *Listeria monocytogenes* in suspension, followed by catching by ELISA-plate immobilised rabbit anti-mouse immunoglobulin antibody.

Experimental

General: All incubations are performed at room temperature with agitation unless otherwise specified.

ELISA-plates (Polysorp from Nunc) were coated with rabbit anti-mouse immunoglubulin antibody (DAKO Z109), 100 µl pr well, diluted 1/100, using 0.1M sodium phosphate, pH 7.2 (=coating buffer) for dilution. The next day, plates were blocked with 3 (w/v) % bovine serum albumin in coating buffer, 400 µl per well for 30 minutes. This was followed by one wash with coating buffer, 400 µl per well >5 minutes. Simultaneously, suspensions of washed live or dead (heat-killed) *Listeria monocytogenes* in various dilutions (see below) in coating buffer were incubated overnight with HRP-B4 at 1/100 in Eppendorf tubes that had previously been coated with 3 (w/v) % BSA for 30 minutes. After this incubation, cells were washed twice in coating buffer, resuspending by vortexing vigorously between centrifugations. Hereafter, plates were incubated with the HRP-B4-incubated cell suspensions for 3 hours. After 4 times wash with 0.1M sodium phosphate, 0.5M NaCl, 0.1 (v/v) % Tween 20, pH 7.2 (using a manual plate-washing device filling wells completely and discarding the liquid again after a few seconds), plates were developed with orthophenylenediamine 8 mg/15 ml (buffer containing tablets from Kem-En-Tec A/S) and hydrogen peroxide, 5 µl 30% for 25 minutes (100 µl per well) until it was stopped with 100 µl 1M sulfuric acid. Absorbance was read in a Bio Rad model 450 microplate reader at 490 nm.

Details: Cells were incubated undiluted (corresponding to $1.9 \times 10^9$ cells/ml), and diluted 1/50 and 1/500 in coating buffer.

Data

|  | Live cells: | Dead Cells: |
| --- | --- | --- |
| undiluted | 2.299 | 0.573 |
| 1/50 | 1.063 | 0.618 |
| 1/500 | 0.669 | 0.733 |
|  | (n = 4) | (n = 4) |

Conclusions

In this system, discrimination is seen to the 1/50 level (corresponds to $3.8 \times 10^7$ cells/ml).

EXAMPLE 8

Detection of B4-catched Cells by Lysis and DNA-extraction Followed by PCT and a Digoxigenin-Antidigoxigenin Visualization System Aim To discriminate between live and dead *Listeria monocytogenes* cells by subjecting B4-antibody-bound cells to lysis followed by PCR using biotinylated primers and digoxigenin-11-dUTP according to the procedure of Holmstrøm, K. L. Rossen and O. F. Rasmussen. Analytical Biochemistry 209,000-000 (1993) in press: A Highly Sensitive and Fast Non-radioactive Method for Detection of Polymerase Chain Reaction Products.

Experimental

General

PCR's were performed according to Holmstrøm et al. 1993, using 5 µl samples and a total reaction volume of 100 µl. Primers were specific for *Listeria monocytogenes* (Holmstrøm et al.) and were obtained commercially, one of them also as the biotinylated oligonucleotide.

Details

ELISA-plates (Maxisorp from Nunc) were coated with B4 antibody, 400 µl per well, diluted 1/50, using 0.1M sodium phosphate, pH 7.2 (=coating buffer) for dilution. Plates were incubated overnight at +4° C.

Plates were blocked with 3 (w/v) % Bovine Serum Albumin (BSA) in coating buffer, 400 µl per well for 30 minutes. This was followed by three washes of 1 minute each with 0.1M sodium phosphate, 0.5M NaCl, 0.1(w/v) % Tween 20, pH 7.2 (=washing buffer), using a manual plate-washing device filling wells completely and discarding the liquid after approximately 1 minute.

Then plates were incubated with live or dead (heat-treated) *Listeria monocytogenes* respectively, diluted in coating buffer (see scheme below) for 1 hour.

After 3 times washing with washing buffer, cells were dissociated from B4 by adding to each well 100 µl 0.05M NaOH, 0.25% SDS, and incubating at room temperature for 20 minutes. The reaction mixture was then transferred to eppendorf tubes and the cells were lysed by incubating at 90° C. for 15 minutes. These samples were subjected to PCR, using 5 µl of each sample to 95 µl PCR-mastermix.

The PCR-products were analyzed by catching biotinylated DNA (PCR-samples diluted in 1/20 in coating buffer)

by a streptavidin-coated ELISA-plate followed by detection of PCR-products by an alkaline phosphatase-conjugated anti-digoxigenin antibody from Boehringer Mannheim (no. 1093274), developed by 4-methylumbelliferylphosphate (Kem-En-Tec A/S), and read as fluorescence intensity as described by Holmstrøm et al. 1993.

Data

| CELLS | INTENSITY |
|---|---|
| live, undiluted (1.9 × 10$^9$ cells/ml) | 0.90 |
| live, 1/10 | 0.70 |
| live, 1/100 | 0.45 |
| dead, 1/10 | 0.27 |
| negative PCR-control[1] | 0.22 |
| negative ELISA-control[2] | 0.21 |
| substrate control | 0.20 |

[1]No template added in PCR. Water used as negative control
[2]No PCR-produce added in analytical ELISA Conclusion Dead cells give a fluorescence intensity close to that of the negative controls, whereas live cells give significantly higher fluorescence intensities. Live vs. dead *Listeria monocytogenes* discrimination by B4 is clearly demonstrated.

I claim:

1. A method of detecting the presence or absence of a viable microorganism in a sample which has been subjected to a process using an antibody which specifically recognizes and binds viable microorganisms, comprising the steps of: contacting the sample with an antibody which specifically recognizes and binds an indicator epitope found only on a surface of an intact viable microorganism and does not bind dead but intact organisms killed by said process, and subsequently optionally eluting the captured microorganism and/or detecting or identifying said microorganism.

2. A method according to claim 1, including the steps of:
   a) capturing organisms in the sample with the antibody which is bound to a solid phase before or after specific binding with the organism has taken place,
   b) washing the solid phase to remove non-specifically bound material, and
   c) detecting the organism.

3. A method according to claim 1 wherein detection of the microorganism includes identification and/or amplification of the nucleic acid in the organism using a detection or amplification system incorporating known oligonuclotides or analogues of nucleic acid.

4. A method according to claim 1, wherein the antibody is bound to a high surface area solid phase and the microorganism is present in a liquid sample.

5. A method according to claim 1, wherein the microorganism is a bacterium, a fungus or a virus.

6. A method according to claim 5, wherein the microorganism is *Listeria monocytogenes*.

7. A method according to claim 1, wherein said process is heat treatment and the indicator epitope is a heat labile epitope found on the surface of viable Listeria cells.

8. A method according to claim 1, wherein the antibody is specific for the detection of viable Listeria cells.

9. A method according to claim 1, wherein the antibody is produced from the cell line BAC01A 3B4A3, ECACC accession no. 91081525.

10. Antibodies from the cell line BACO1A 384A3, ECACC accession no. 91081525.

11. The cell line BACO1A 384A3, ECACC accession no. 91081525.

12. The method according to claim 1 wherein the microorganism is selected from the group consisting of eucaryotic cells, procaryotic cells and viruses.

13. A kit for the detection of viable microorganisms in a sample subjected to a process, the kit comprising a solid phase coated with an antibody, which specifically recognizes and binds an indicator epitope found only on a surface of an intact viable microorganism and which does not bind dead but intact microorganisms killed by said process, buffers for dispersing the sample, washing buffers, elution and/or disruption buffers to expose the nucleic acid in the captured microorganism, hybridisation or amplification reagents to detect or amplify the exposed nucleic acid, or a labelled second antibody to bind to the captured microorganism in an immunoassay, reagents to detect the hybridised probe or the amplified nucleic acid or nucleic acid analogue sequence or the labelled antibody in an immunoassay.

14. The method according to claim 4, wherein the high surface area solid phase is a nylon mesh or a microparticle.

* * * * *